(12) United States Patent
Schebesta et al.

(10) Patent No.: US 8,836,938 B2
(45) Date of Patent: Sep. 16, 2014

(54) STANDARD FOR WAVELENGTH AND INTENSITY FOR SPECTROMETERS

(75) Inventors: Wilhelm Schebesta, Jena (DE); Nico Correns, Weimar (DE); Lutz Freytag, Jena (DE); Michael Rode, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 12/122,861

(22) Filed: May 19, 2008

(65) Prior Publication Data

US 2009/0002696 A1    Jan. 1, 2009

(30) Foreign Application Priority Data

Jun. 26, 2007   (DE) .......................... 10 2007 029 405

(51) Int. Cl.
| | | |
|---|---|---|
| G01J 1/10 | (2006.01) | |
| G01N 21/27 | (2006.01) | |
| G01N 21/35 | (2014.01) | |

(52) U.S. Cl.
CPC ............ G01N 21/278 (2013.01); G01N 21/359 (2013.01)
USPC ..... 356/243.1; 356/326; 356/328; 250/252.1; 250/574; 436/171; 600/310

(58) Field of Classification Search
USPC .............. 356/243.1, 243.5; 250/338.1, 252.1
See application file for complete search history.

(56) References Cited

U.S. PATENT DOCUMENTS

| | | | |
|---|---|---|---|
| 5,523,054 A * | 6/1996 | Switalski et al. ................ 422/58 |
| 6,249,343 B1 | 6/2001 | Wang et al. | |
| 6,527,410 B2 * | 3/2003 | Yamaguchi .................... 362/243 |
| 7,923,114 B2 * | 4/2011 | Myli et al. ..................... 428/426 |
| 2003/0214718 A1 * | 11/2003 | Kaminsky et al. ............. 359/599 |
| 2004/0070041 A1 * | 4/2004 | Obayashi et al. ............. 257/437 |
| 2004/0169857 A1 * | 9/2004 | Acosta et al. ................. 356/328 |
| 2005/0122512 A1 | 6/2005 | Grot et al. | |
| 2005/0163958 A1 * | 7/2005 | Nakatsugawa ................ 428/40.1 |
| 2006/0066856 A1 * | 3/2006 | Cummings et al. ........... 356/402 |
| 2006/0141243 A1 * | 6/2006 | Ibuki ............................. 428/334 |
| 2007/0146887 A1 * | 6/2007 | Ikeda et al. .................... 359/586 |
| 2007/0206286 A1 * | 9/2007 | Fukushige et al. ............ 359/580 |
| 2007/0236636 A1 * | 10/2007 | Watson et al. ................ 349/117 |

FOREIGN PATENT DOCUMENTS

| | | |
|---|---|---|
| DE | 698 36 166 | 2/2007 |
| EP | 1 696 224 | 2/2006 |

OTHER PUBLICATIONS

Stefan Bäumer, "Handbook of Plastic Optics", pp. 128-129, 2005 Wiley-VCH Verlag GmbH & Co. KGaA Weinheim, Phillips Center of Industrial Technology (CFT), Industrial Optics, Eindhoven, The Netherlands.

J.Y. Shin et al., International Union of Pure and Applied Chemistry Polymer Division (IUPAC Technical Report) "Chemical Structure and Physical Properties of Cyclic Olefin Copolymers", Pure Appl. Chem., vol. 77 No. 5, pp. 801-814, 2005, The Chinese Academy of Sciences, Beijing 100080, China.

European Pharmacopoeia 5.0, "2.2.40. Near-infrared spectrophotometry", pp. 59 to 61, year on p. 59 show Jan. 2005.

European Pharmacopoeia 5.0, "2.2.40. Near-infrared spectrophotometry", pp. 59 to 63, year show on p. 59 as Jan. 2005.

* cited by examiner

*Primary Examiner* — Tarifur Chowdhury
*Assistant Examiner* — Isiaka Akanbi
(74) *Attorney, Agent, or Firm* — Frommer Lawrence & Haug LLP

(57) ABSTRACT

The description relates to a standard for wavelength and intensity for spectrometers, particularly for calibrating and testing measurement heads in spectrometers which are usable primarily in the near infrared region (NIR) of the spectrum. The standard comprises a holder and a plate body arranged in the holder. The plate body is made of transparent plastic with high strength and dimensional stability over a large temperature range. The plastic has distinct absorption bands throughout the entire NIR range and has a chemical structure and composition ensuring an extensive moisture barrier against water absorption and water release in a reliable and stable manner over time. The plate body advantageously comprises an amorphous, transparent copolymer based on cyclic and/or linear olefins.

17 Claims, 1 Drawing Sheet

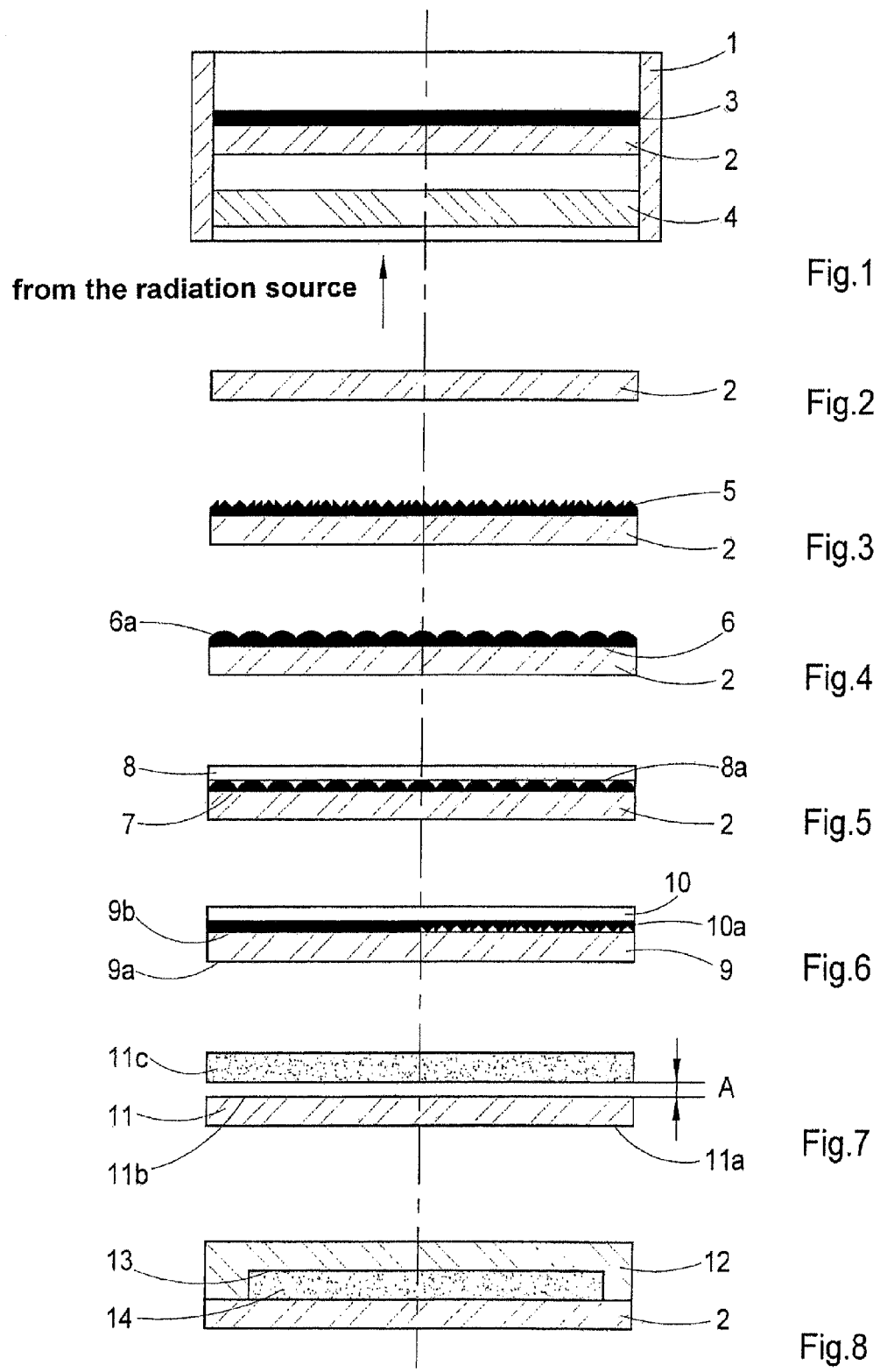

STANDARD FOR WAVELENGTH AND INTENSITY FOR SPECTROMETERS

CROSS-REFERENCE TO RELATED APPLICATION

This application claims priority of German Application No. 10 2007 029 405.2, filed Jun. 26, 2007, the complete disclosure of which is hereby incorporated by reference.

BACKGROUND OF THE INVENTION a) Field of the Invention

The invention is directed to a standard for wavelength and intensity for spectrometers, particularly for the physical and chemical analysis of substances and for determining the characteristics of these substances and for process control, in particular in the chemical industry. This standard is preferably provided for calibrating and testing measurement heads for spectrometers which are used in the near infrared range (NIR) of the spectrum and in transmission measurements and measurements in reflected light.

b) Description of the Related Art

The disclosure of European Pharmacopoeia 5.0, "2.2.40. Near-infrared spectrophotometry", pages 59 to 61, includes arrangements for calibrating spectrometers for measuring substances and samples with radiation in the near infrared region of the spectrum with wavelengths between 780 nm and 2500 nm. Qualitative and quantitative physical and chemical information about the substances and samples being examined can be obtained in this way. However, there is no direct comparison of the spectrum of a substance that is tested with a reference spectrum of a chemical reference substance as is conventional in IR absorption spectroscopy.

It is well known in infrared spectroscopy to apply the following measurement methods: transmission measurements, measurements with diffuse reflection, and a combined method in which a diffusely reflecting reflector is arranged behind the substance or sample to be tested, e.g., liquids and solids which are transparent for infrared (IR) radiation of the wavelengths in question.

Measurements with diffuse reflection are generally applied in solids. In this connection, it must be ensured that the measurement conditions are as reproducible as possible from one sample to the next. The reflected radiation of a reflecting background reference (standard) is scanned (tested) in order to obtain a wavelength standard as a reference base for the sample measurements. Materials used for the standard include ceramic materials, perfluoropolymers, methyl chlorides, or gold. It is disadvantageous that only spectra possessing the same optical properties can be measured and compared to standards. Further, the particle size, water absorption and state of solubility must be taken into account.

In the combined method mentioned above, a reflector is arranged behind the sample to increase the optical path length. The sample is tested in a cell with a suitable diffusely reflecting reflector comprising either a suitable metal or an inert material such as, e.g., titanium dioxide ($TiO_2$) which does not absorb radiation in the infrared spectral region in question and retains its properties without being influenced by environmental conditions such as, e.g., humidity, over a long period of time.

OBJECT AND SUMMARY OF THE INVENTION

Accordingly, it is the primary object of the invention to provide a standard for wavelength and intensity for NIR spectrometers which is stable over time, economical, and easy to handle in the entire near infrared region (NIR) of the spectrum and which can be used as a standard in transmission and reflection for testing and calibrating this spectrometer.

According to the invention, this object is met by a standard for wavelength and intensity for spectrometers, particularly for calibrating and testing measurement heads in spectrometers which are usable primarily in the near infrared region of the spectrum comprising a holder and a plate body being arranged in the holder. The plate body is being made of transparent plastic with high strength and dimensional stability over a large temperature range. The plastic has distinct absorption bands throughout the entire NIR range and has a chemical structure and composition ensuring an extensive moisture barrier against water absorption and water release in a reliable and stable manner over time.

In order to obtain clear and evaluable absorption bands for the measurements, it is advantageous when the plate body comprises an amorphous, transparent copolymer based on cyclic and/or linear olefins.

In this regard, it is advantageous that the plate body is constructed as a transparent plate, one of whose surfaces is coated with a diffusely reflecting layer.

It has proven particularly advantageous when the diffusely reflecting layer comprises titanium dioxide or a paint containing titanium dioxide.

It may also be advantageous when the plate has a roughened surface that is coated with a suitable well-reflecting metal.

In this regard, it is advantageous when the roughened surface is coated with gold.

In order to achieve a diffuse reflection, one surface of the plate can also be provided with a metal-coated microlens array.

Further, it can be advantageous that the plate body is connected to a reflecting metal plate which is fixedly arranged at, or arranged at a distance A from, the surface of the plate that is roughened or provided with a microlens array.

In an advantageous embodiment form of the standard, the plate body has two oppositely located smooth, transparent surfaces, and a metal plate which is roughened or coated with $TiO_2$ is provided, and the roughened surface or coated surface of the metal plate fixedly contacts, or is arranged at a distance from, one of the smooth surfaces of the plate body.

Further, it can be advantageous that the plate body is made of a plastic with an admixture of about 3% $TiO_2$.

Another advantageous embodiment form of the standard comprises a plate body in the form of a purely plastic plate and a plastic plate mixed with $TiO_2$, and the distance between the two plastic plates is dimensioned in such a way that there is no interference between them.

In order to carry out transmission measurements, it is advantageous when the plate body is made of transparent plastic and the surfaces of the plate body are not coated.

To protect against environmental influences and against wear, it is advantageous when the holder of the standard is closed outwardly by a cover plate of tempered glass or by a sapphire disk.

The invention will be described more fully in the following with reference to an embodiment example.

BRIEF DESCRIPTION OF THE DRAWINGS

In the drawings:

FIG. 1 shows the basic construction of a standard for wavelength and intensity;

FIG. 2 shows a plate body with a diffusely reflecting layer;

FIG. 3 shows a plate body with a roughened reflecting surface;

FIG. 4 shows a plate body with a reflecting microlens array;

FIG. 5 shows a plate body with a diffusely reflecting metal plate;

FIG. 6 shows a plate body with a roughened metal plate and a metal plate which is coated with $TiO_2$;

FIG. 7 shows a plate body with a plastic plate that is mixed with $TiO_2$; and

FIG. 8 shows a plate body and a plate with a $TiO_2$ powder sandwiched in between.

DESCRIPTION OF THE PREFERRED EMBODIMENTS

FIG. 1 is a sectional view of a standard for wavelength and intensity for spectrometers which is suitable in particular for calibrating and testing measurement heads for spectrometers working primarily with radiation in the near infrared region (NIR) of the spectrum. This standard advantageously has a holder 1 and a plate body 2 which is arranged in the holder 1 and which is made of a suitable transparent plastic with high strength and dimensional stability over a large temperature range. The plastic has easily evaluable, distinct absorption bands throughout the entire NIR range and has a chemical structure and composition ensuring a very low moisture absorption or water absorption from the environment and a very low release of moisture or water to the environment in a reliable and stable manner over a long duration. This must be guaranteed in order to maintain a constant absorption band structure of the standard over long periods of time. Suitable plastics for the plate body 2 are, for example, cyclo olefin copolymers in the form of amorphous, transparent copolymers based on cyclic and/or linear olefins, e.g., Zeonex® Cyclo Olefin Polymer (COC) based on norbornene derivatives.

To carry out measurements and calibrations in reflected light, a diffusely reflecting layer 3, which advantageously comprises titanium dioxide ($TiO_2$) or $TiO_2$-containing paint, is applied to the surface of the plate body 2 remote of the radiation source as is shown in FIG. 1. For measurements and calibrations of this type, the thickness of the plate is advantageously at least 4 mm in order to obtain easily evaluable absorption bands of the plate body 2 which are well-suited to the calibration of IR spectroscopes.

When a standard is provided for transparency measurements (FIG. 2), an uncoated plate of suitable thickness is arranged in the holder 1. The plate thickness should advantageously be at least 8 mm to obtain easily evaluable absorption bands at the passage of radiation.

The holder 1 can be closed on one or both sides by closing plates 4 to protect against environmental influences. FIG. 1 shows only one closing plate 4. The material for the closing plate 4 must be resistant to wear and to solvents and acids. Tempered glass or sapphire is advantageously provided as this material. The distance of the closing plate 4 from the plate body 2 is advantageously dimensioned in such a way that no interference can occur between these plates 2 and 4.

FIG. 3 shows a plate body 2 whose surface 5 remote of the radiation source is roughened by sandblasting or by a suitable tool and which is coated with a suitable reflecting metal, advantageously gold.

FIG. 4 shows a plate body 2 with a reflecting surface 6 on which a metal-coated microlens array 6a is formed.

FIG. 5 shows an embodiment form with a plate body 2 having a surface 7 that is roughened or on which a microlens array 7a is formed. A reflecting plate 8 of metal or plastic whose reflecting surface 8a adjoins the plate body 2 is arranged at the surface 2 of the plate body 2 remote of the radiation source.

In the embodiment form according to FIG. 6, a plate body 9 has two oppositely located smooth, transparent surfaces 9a and 9b. The plate body 9 is connected to a plate 10 that is provided with a roughened or titanium dioxide-coated surface 10a. The surface 10a is reflecting. The plate 10a can also be provided with a reflecting microlens array. The surface 10a of the plate 10 faces the plate body 9. Plates 9 and 10 can contact one another. However, they can also be arranged at a distance A from one another in the holder 1, in which case it must be ensured that interference is prevented between the two plates 9 and 10.

FIG. 7 shows a plate body which is constructed as a plastic plate 11 and which has two smooth, transparent surfaces 11a and 11b. A plastic plate 11c is provided at a distance A, a determined amount of titanium dioxide being embedded therein to achieve a diffuse reflection in the interior of the plastic plate 11. About 3% $TiO_2$ is advantageously added to the plastic plate 11c.

FIG. 8 shows a standard for measurements in reflecting light which comprises a plate body 2 and a plate 12 which is connected to the latter. The plate 12 has a recess 13 at its side facing the plate body 2. $TiO_2$ powder 14 is advantageously arranged in this recess 13.

While the foregoing description and drawings represent the present invention, it will be obvious to those skilled in the art that various changes may be made therein without departing from the true spirit and scope of the present invention.

REFERENCE NUMBERS 1 holder
2 plate body
2a; 2b surface
3 layer
4 closing plate
5 surface
6 surface
6a microlens array
7 structured surface
7a microlens array
8 reflecting plate
8a reflecting surface
9 plate body
9a; 9b transparent surface
10 plate
10a surface
11; 11c plastic plate
11a; 11b surface
12 plate
13 recess
14 $TiO_2$ powder

What is claimed is:

1. A method for calibrating a spectrometer, comprising:
providing a standard for wavelength and intensity for calibrating the spectrometer comprising:

a transparent plastic plate body of at least 4 mm comprising an amorphous, transparent copolymer based on at least one of cyclic and linear olefins, the plate body having distinct absorption bands in the infrared range suitable for calibrating a spectrometer; and a diffusely reflecting body arranged at one side of the plate body calibrating a spectrometer using the standard.

2. The method of claim 1, wherein the plate body has a thickness of at least 8 mm.

3. The method of claim 1, wherein the diffusely reflecting layer comprises a paint containing titanium dioxide.

4. The method of claim 1; wherein the plate body has a roughened surface that is coated with a well-reflecting metal as the diffusely reflecting body.

5. The method of claim 4; wherein the roughened surface is coated with gold.

6. The method of claim 1; wherein one surface of the plate body is provided with a metal-coated micro lens array as the diffusely reflecting body.

7. The method of claim 1; wherein the plate body is connected to a reflecting metal plate which is fixedly arranged at, or which is arranged at a distance A from, the surface of the plate body that is roughened or that is provided with a microlens array.

8. The method of claim 1, wherein the plate body has two oppositely located smooth, transparent surfaces, and in that a plate which is roughened or coated with $TiO_2$ is provided, and the roughened surface or coated surface of the plate fixedly contacts, or is arranged at a distance from, one of the smooth surfaces of the plate body.

9. The method of claim 1, wherein the plate body is made of a plastic with an admixture of about 3% $TiO_2$.

10. The method of claim 1, wherein the standard comprises a purely plastic plate and a plastic plate mixed with $TiO_2$, wherein a body-free distance A between the two plastic plates is dimensioned in such a way that there is no interference between them.

11. The method of claim 1, wherein the plate body is made of transparent plastic in order to carry out transmission measurements, wherein the surfaces of the plate body are not coated.

12. The method of claim 1, wherein the plate body and the diffusely reflecting body are arranged in a holder.

13. The method of claim 12; wherein the holder is closed outwardly by a cover plate.

14. The method of claim 1; wherein one of the plate body's surfaces is coated with a diffusely reflecting layer as the diffusely reflecting body.

15. The method of claim 1, wherein the copolymer is Zeonex.

16. The method of claim 1, wherein the copolymer is based on a norbonene olefin.

17. The method of claim 1, wherein the diffusely reflecting body is a plate having a reflecting surface facing the plate body.

* * * * *